US 10,881,546 B2

(12) United States Patent
Hansen et al.

(10) Patent No.: US 10,881,546 B2
(45) Date of Patent: Jan. 5, 2021

(54) BODY SIDE MEMBER OF AN OSTOMY APPLIANCE

(71) Applicant: Coloplast A/S, Humlebaek (DK)

(72) Inventors: Michael Hansen, Gilleleje (DK); Birthe Vestbo Andersen, Espergaerde (DK)

(73) Assignee: Coloplast A/S, Humlebaek (DK)

( * ) Notice: Subject to any disclaimer, the term of this patent is extended or adjusted under 35 U.S.C. 154(b) by 420 days.

(21) Appl. No.: 15/769,659

(22) PCT Filed: Oct. 19, 2016

(86) PCT No.: PCT/DK2016/050337
§ 371 (c)(1),
(2) Date: Apr. 19, 2018

(87) PCT Pub. No.: WO2017/067560
PCT Pub. Date: Apr. 27, 2017

(65) Prior Publication Data
US 2018/0311066 A1 Nov. 1, 2018

(30) Foreign Application Priority Data

Oct. 20, 2015 (DK) .................................. 2015 70677
Sep. 20, 2016 (DK) .................................. 2016 70745

(51) Int. Cl.
A61F 5/443 (2006.01)
A61F 5/445 (2006.01)
A61F 5/44 (2006.01)
A61F 5/448 (2006.01)

(52) U.S. Cl.
CPC ............ A61F 5/443 (2013.01); A61F 5/4401 (2013.01); A61F 5/445 (2013.01); A61F 5/448 (2013.01)

(58) Field of Classification Search
CPC combination set(s) only.
See application file for complete search history.

(56) References Cited

U.S. PATENT DOCUMENTS

| 5,445,597 | A | 8/1995 | Clark et al. |
| 5,662,626 | A | 9/1997 | Ruotoistenmaaki et al. |
| 5,902,433 | A | 5/1999 | Becher et al. |
| 6,544,241 | B2 * | 4/2003 | Morton ................ A61F 5/4407 604/317 |
| 7,396,976 | B2 * | 7/2008 | Hurwitz .............. A61F 13/0203 602/41 |

(Continued)

FOREIGN PATENT DOCUMENTS

| CN | 1764426 A | 4/2006 |
| CN | 101437479 A | 5/2009 |

(Continued)

Primary Examiner — Guy K Townsend
(74) Attorney, Agent, or Firm — Coloplast Corp., Coloplast A/S; Nick Baumann

(57) ABSTRACT

An ostomy appliance comprising a body side member (20) for attachment to a skin surface of a user. The body side member includes a backing layer (22), an adhesive layer (24), and at least one release liner (38). The release liner is at least partly embossed (40) to form interconnected cavities (42) between the release liner and the adhesive surface. When fluid is distributed into the cavities, the adhesive surface is wetted.

12 Claims, 2 Drawing Sheets

(56) References Cited

U.S. PATENT DOCUMENTS

| | | | |
|---|---|---|---|
| 8,453,348 B2* | 6/2013 | Fox | B29D 35/142 |
| | | | 36/44 |
| 8,708,987 B2* | 4/2014 | Cramer | A61F 5/443 |
| | | | 604/344 |
| 8,946,499 B2* | 2/2015 | Iyer | A61L 15/44 |
| | | | 602/41 |
| 8,957,277 B2* | 2/2015 | Carty | A61L 15/42 |
| | | | 602/41 |
| 9,168,180 B2* | 10/2015 | Ha | A61F 13/0289 |
| 10,369,058 B2* | 8/2019 | Ha | A61F 13/0008 |
| 2002/0013558 A1* | 1/2002 | Morton | A61F 5/445 |
| | | | 604/332 |
| 2003/0109838 A1* | 6/2003 | Morton | A61F 5/445 |
| | | | 604/334 |
| 2003/0170308 A1* | 9/2003 | Cleary | A61K 8/0208 |
| | | | 424/486 |
| 2004/0216833 A1 | 11/2004 | Fleming et al. | |
| 2006/0195053 A1* | 8/2006 | Oelund | A61F 5/448 |
| | | | 602/43 |
| 2007/0027434 A1* | 2/2007 | Pedersen | A61F 5/448 |
| | | | 604/333 |
| 2009/0259192 A1* | 10/2009 | Fabo | B32B 7/12 |
| | | | 604/180 |
| 2010/0022933 A1* | 1/2010 | Oelund | A61F 5/448 |
| | | | 602/54 |
| 2010/0318052 A1* | 12/2010 | Ha | A61F 13/0008 |
| | | | 604/385.01 |
| 2010/0324507 A1 | 12/2010 | Maier | |
| 2011/0213322 A1* | 9/2011 | Cramer | A61F 5/443 |
| | | | 604/344 |
| 2012/0123220 A1* | 5/2012 | Iyer | A61L 15/42 |
| | | | 600/300 |
| 2012/0220966 A1 | 8/2012 | Lundholt et al. | |
| 2012/0323192 A1* | 12/2012 | Willoughby | A61F 5/44 |
| | | | 604/337 |
| 2013/0123678 A1* | 5/2013 | Carty | A61F 13/0253 |
| | | | 602/54 |
| 2014/0316360 A1* | 10/2014 | Ekfeldt | A61F 5/443 |
| | | | 604/344 |
| 2016/0038345 A1* | 2/2016 | Ha | A61F 13/02 |
| | | | 602/46 |
| 2018/0311066 A1* | 11/2018 | Hansen | A61F 5/445 |

FOREIGN PATENT DOCUMENTS

| | | |
|---|---|---|
| CN | 101939393 A | 1/2011 |
| RU | 2525209 C2 | 8/2014 |
| RU | 2536708 C2 | 12/2014 |
| RU | 2013132977 A | 1/2015 |
| RU | 2566078 C2 | 10/2015 |
| WO | 9938929 A1 | 8/1999 |
| WO | 0112116 A1 | 2/2001 |
| WO | 03061720 A1 | 7/2003 |
| WO | 11054434 A1 | 5/2011 |

* cited by examiner

BODY SIDE MEMBER OF AN OSTOMY APPLIANCE

SUMMARY

Disclosed is a body side member of an ostomy appliance for attachment to a skin surface of a user. The body side member includes a backing layer, an adhesive layer, and at least one release liner. The release liner comprises an embossed surface facing the adhesive layer.

BRIEF DESCRIPTION OF THE DRAWING

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated, as they become better understood by reference to the following detailed description. The elements of the drawings are not necessarily to scale relative to each other. Like reference numerals designate corresponding similar parts.

DETAILED DESCRIPTION

One aspect provides a body side member of an ostomy appliance according to the appended claim 1.

It may be desired to apply a liquid substance to the adhesive skin-facing surface of a base plate before application of the plate. Such liquid may contain an active agent or medicament or it may be a composition capable of altering the properties of the adhesive surface, for example by changing viscosity, adhesive tack or the like. However, it may be difficult to apply a liquid to an adhesive surface in a hygienic way, using a wipe to wet the surface may result in fingers touching the adhesive as well as residues from the wipe (fibres etc.) may stick to the adhesive surface as well as it may be difficult to ensure that the entire desired surface is adequately wetted.

In the following detailed description, reference is made to the accompanying drawings, which form a part hereof, and in which is shown by way of illustration of specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

When referring to the proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side the side furthest away from the user in use.

"Release liner" is intended to define a liner covering the proximal (skin contacting) side of the body side member, which ensures at least that the properties of the adhesive are preserved and that the adhesive surface is not laid open until just before use.

Figure 1:
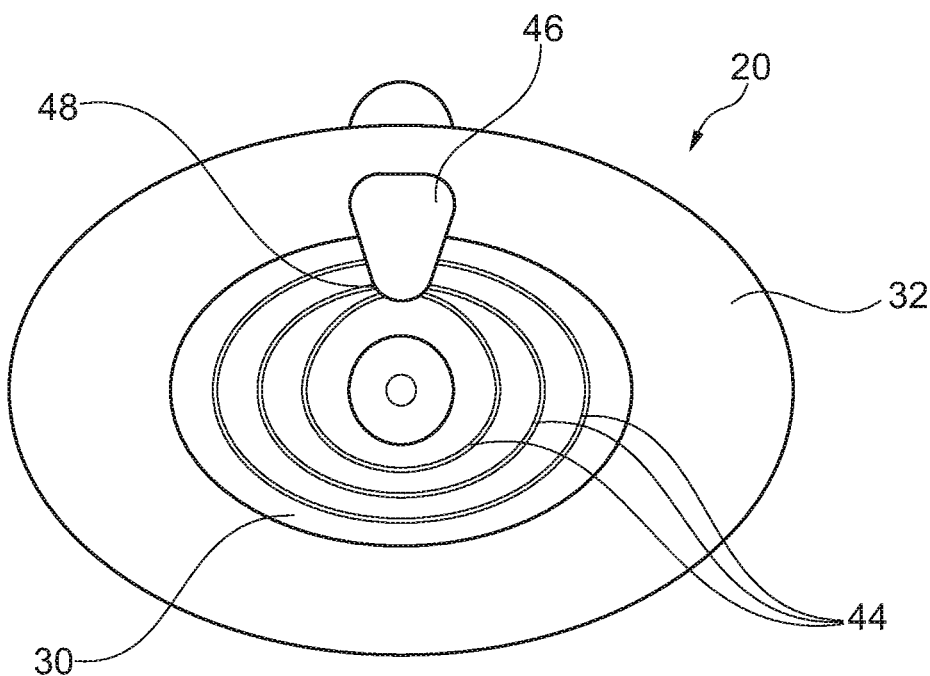
FIG. 1 is a schematic, proximal view of one embodiment of a body side member of an ostomy appliance.
Figure 2:
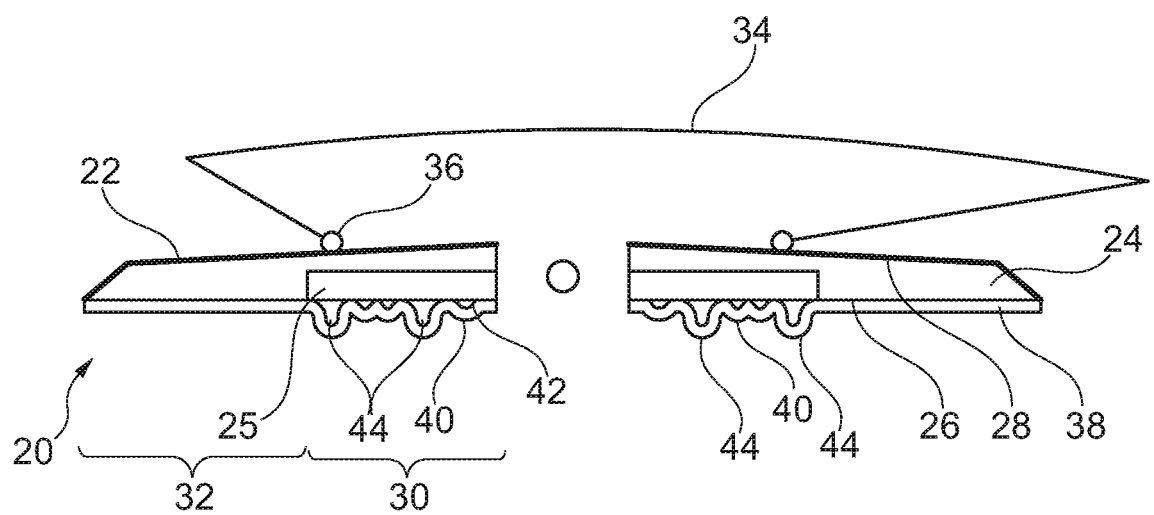
FIG. 2 is a schematic, cross-sectional view illustrating an embodiment of the body side member including a collection bag.

In FIGS. 1 and 2 are shown a proximal and a cross-sectional view of an embodiment of a body side member 20 of an ostomy appliance. The body side member 20 includes a backing layer 22 and an adhesive layer 24. The adhesive layer is having a proximal surface 26 and a distal surface 28. The adhesive surface 26 is defined by a first central zone 30 circumferencing a stoma-receiving through-going hole O defining an inner boundary of said first zone 30, said first zone 30 being adjacent to and extending radially from said through-going hole O. A second zone 32 is surrounding said first zone 30, an outer boundary of the second zone 32 is defining an outer boundary of the body side member 20. In embodiments, the adhesive layer 24 comprises one or more different adhesive materials provided in a side-by-side manner. In embodiments, the different adhesive materials of the adhesive layer 24 are provided in a layered structure. In embodiments, the different adhesive materials of the adhesive layer 24 are provided primarily side-by-side, but with some overlapping portions. In FIG. 2 is shown an embodiment with a second adhesive 25 covering the proximal surface of the first zone.

On the distal surface of the backing layer 22 is arranged a collection bag 34. In embodiments, the bag 34 is attached to the backing layer 22 at a coupling point 36, either in the form of a releasable mechanical or adhesive coupling (a so-called two-piece device) or by a non-releasable welding or adhesive (a so-called one-piece device).

The proximal surface 26 of the adhesive layer is provided with a release liner 38 protecting the adhesive surface 26 before use. At least a part of a distal surface of the release liner is embossed 40 to define a plurality of interconnected cavities 42 between the proximal adhesive surface and a proximal surface of the release liner 40. The embossed area of the release liner comprises at least one channel 44 such as two or more channels 44. In embodiments, the cavities 42 are distributed in a random or organized pattern over at least a selected part of the release liner. In embodiments, the channels are distributed over the part of the release liner covering the first central zone 30 of the adhesive layer. In embodiments, the channels 44 have a larger volume than the interconnected cavities 42, herein meant as the channels 44 are able to transport more liquid than the cavities 42, so the liquid is faster and more efficiently distributed over the adhesive surface 26 through the channels 44 and then further distributed through the interconnected cavities 42. The channels 44 may be substantially homogeneously distributed over the embossed surface in order to provide a fast initial distribution of the liquid. In embodiments, the channels and the interconnected cavities are defined on three sides by the release liner and on the third side by the adhesive layer.

The release liner 38 comprises a reservoir 46 containing liquid. The reservoir 46 is configured to be brought into liquid connection with the channels 44 on demand. In embodiments, the reservoir 46 is provided with one or more outlets 48. In embodiments, the outlet 48 is closed with a rupturable membrane or seal (not shown) that is configured to open when the reservoir 46 is exposed to pressure from the outside, such as by pressing a finger towards an outer surface of the reservoir 46. When the outlet 48 is opened (and the reservoir 46 is squeezed), liquid from the reservoir 46 is dispensed into the channels 44 and from the channels distributed further into the interconnected cavities 42. In this way, the adhesive surface 26 under the embossed part of the release liner is wetted by the liquid. In embodiments, the volume of the reservoir 46 corresponds substantially to the combined volume of the channels 44 and the cavities 42. In this way, a surplus of liquid is avoided and the risk of liquid dripping from the body side member 20 is minimized.

It should be understood that the interconnected cavities and the channels are two different structures. In embodiments, the cavities provide the distal surface of the release liner with a creased-like surface, being a micro-structure of interconnected cavities. Liquid can diffuse into these cavities, but due to the small size and volume, it may take time and it may be difficult to reach and wet the entire surface in reasonable time if only the cavities are used as liquid distribution system. Hence, a number of channels, being a macro-structure having a substantially larger volume are introduced. The channels are able to, in a fast and efficient manner to transport the liquid over the adhesive surface, and the channels being in liquid connection with the cavities, the liquid will diffuse from the channels into the cavities and wet the adhesive surface.

The interconnected cavities and the channels are defined as volumes between the proximal surface of the adhesive layer and the embossed distal surface of the release liner. In embodiments, the embossed pattern of cavities has a depth of 1-2% of the thickness of the release liner.

In embodiments, the channels are tube-like structures. In embodiments, the channels have a width of 0.1-1.5 mm, such as 0.5-1 mm. The width is measured in radial direction of the base plate. In embodiments, the channels have a depth of 0.02-0.1 mm, such as 0.04-0.08 mm. The depth is measured in axial direction, being perpendicular to the radial direction. The channels may be provided by thermoforming the release liner and may appear as a depression in the release liner and/or they may appear as a raised portion of the release liner and may therefore in some cases appear higher than the thickness of the release liner. In embodiments, the channels 44 are arranged substantially homogeneously over the release liner. In embodiments, the channels may be arranged as substantially concentric circles, surrounding a through-going hole O of the body side member, as shown in FIG. 1. In embodiments, the channels may be branched to provide a network of channels over the surface.

The body side member 20 includes a through-going opening O extending through the backing layer 22 and the adhesive layer 24. The through-going opening O is surrounded by the first zone 30.

In embodiments, the release liner is embossed in the first zone. The second zone may be smooth (not embossed) and thereby provide a peripheral sealing of the embossed zone. In embodiments, the second zone is embossed. The outer periphery may comprise a smooth zone in order to seal the edge from escaping liquid.

When addressing an embossed release liner herein is to be understood that the release liner has at least one surface (the distal surface facing the adhesive) which is provided with a network of interconnected cavities. These cavities may be provided by embossing or other process giving rise to such cavities in the release liner.

In embodiments, an indicator capable of indicating presence of moisture may be comprised in the body side member. The indicator may provide a visual change such as a colour change when wetted. The presence of an indicator makes it easy for the user to see when the liquid is fully distributed over the surface to be wetted.

Figure 3:
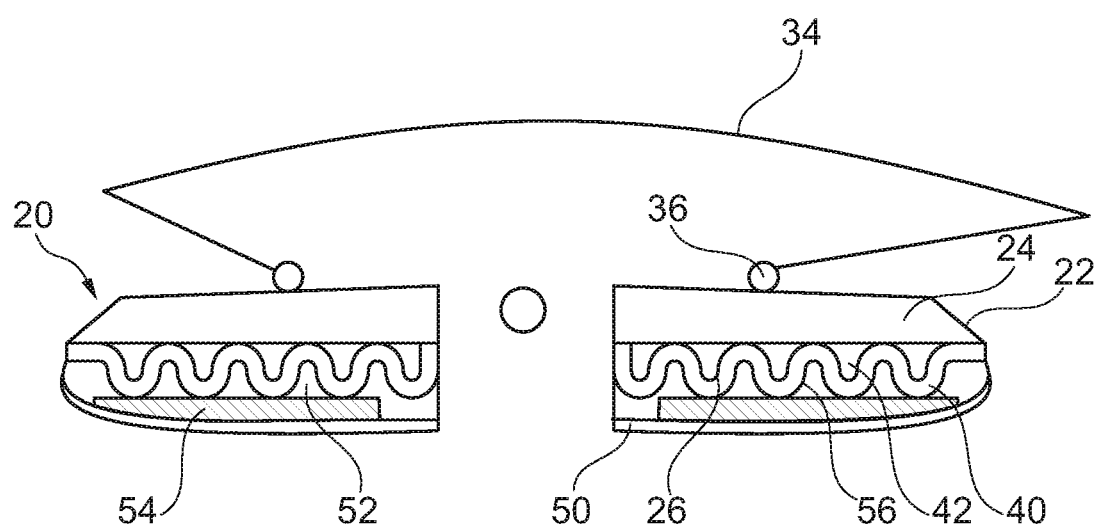
FIG. 3 is a schematic, cross-sectional view illustrating an embodiment of the body side member including a collection bag.

In FIG. 3 is shown a cross-sectional view of an embodiment comprising an absorbent material. The body side member 20 is provided with an embossed release liner 40 facing the adhesive surface 26 and a cover layer located on the proximal surface of the release liner 40. The cover 50 layer is sealed to the release liner 40 along the edge portion to form an enclosure 52. The cover layer is substantially liquid impermeable. In the enclosure is an absorbent material 54. In embodiments, such absorbent material is a wipe, gauze, fabric or foam or it may be in the form of a powder or particles. In embodiments, the release liner is provided with perforations 56 enabling liquid to pass from the cavities 42 and into the absorbent material 54 of the enclosure 52. In this way, the adhesive surface 26 may be wetted and excessive liquid may be soaked up by the absorbent material 54. In embodiments, the release liner 40 is at least partly liquid permeable. The release liner 40 may be made from a porous material or other material being liquid permeable by nature or it may be an impervious layer provided with a plurality of perforations 56 allowing liquid to pass through.

In embodiments, the absorbent material 54 may comprise an indicator changing colour when the material 54 is wetted, making it easy for the user to see when the adhesive is adequately wetted.

In embodiments, the adhesive may be sensitive to direct contact with a specific liquid. The adhesive may change properties by direct contact with this liquid, such as altering the tack or viscosity of the adhesive. In embodiments, the liquid is water.

In embodiments, the adhesive is a silicone pressure sensitive adhesive and the liquid is a solvent selected from a silicone fluid, hexamethyldisiloxane (HMDS), and ethyl acetate. In embodiments, the adhesive is a styrene copolymer pressure sensitive adhesive, such as a mixture of SIS and polyisobutylene, and the liquid is a solvent selected from acetone, THF, ethyl acetate, butyl acetate, and hexane. In embodiments, the adhesive is a polyurethane pressure sensitive adhesive and the liquid is a solvent in the form of THF. In embodiments, the adhesive is an acrylate pressure sensitive adhesive and the liquid is a solvent selected from ethanol and iso-propanol. In embodiments, the adhesive is an EVA pressure sensitive adhesive and the liquid is a solvent selected from THF and iso-propanol. These are just examples of possible combinations of adhesive polymer and liquid solvent types. Other combinations are possible.

Various physical parameters of the adhesive may be changed by activating or re-activating the adhesive by bringing it into contact with the solvent. In embodiments, a property of the adhesive selected from the group consisting of tack and peel force is increased after activation or re-activation. In embodiments, a property of the adhesive selected from the group consisting of viscosity, modulus, shear force, and cohesion is decreased after activation or re-activation.

One aspect provides an ostomy appliance, comprising: a body side member according to claim 1; a stomal output collecting bag; wherein the stomal output bag is fixedly attached to the distal surface of the backing layer of the body side member.

One aspect provides a method of applying an ostomy appliance.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

EXAMPLE

An ostomy base plate comprising a backing layer covered on the proximal surface with an adhesive layer was provided. A release liner in the form of an embossed PE foil having a thickness of 0.045 mm was provided, the foil having an embossed pattern of interconnected cavities of a depth of 2% of the thickness of the foil. Channels having a width of 1 mm and a depth of 0.05 mm was made by running a hot iron over the foil. The channels were distributed evenly over the embossed release liner as shown in FIG. 1. A liquid containing reservoir in the form of two layers of foil welded together was provided on the release liner, the reservoir comprising an outlet that can be opened and thereby be in fluid connection with the channels. The release liner was attached to the proximal surface of the adhesive base plate such that open side of the channel is facing the adhesive surface. When the outlet of the reservoir is opened, for example by pressing the reservoir with a finger, the liquid is flowing into the channels, and from the channel the liquid diffuses into the interconnected cavities, thereby wetting the surface of the adhesive.

The invention claimed is:

1. A body side member of an ostomy appliance, comprising:
   a backing layer having a proximal surface and a distal surface, the proximal surface of the backing layer comprising an adhesive layer, with the adhesive layer being defined by a first zone and a second zone surrounding the first zone,
   a through-going opening extending through the backing layer and the adhesive layer and surrounded by the first zone;
   a release liner covering a proximal adhesive surface of the adhesive layer; and
   a distal surface of the release liner is embossed to define a plurality of interconnected cavities between the proximal adhesive surface and the release liner,
   wherein the release liner comprises a reservoir containing a liquid, the reservoir is configured to dispense the liquid from the reservoir into the interconnected cavities.

2. The body side member of claim 1, wherein the release liner comprises at least one channel connecting the interconnected cavities to the reservoir.

3. The body side member of claim 2, wherein the release liner comprises two or more channels.

4. The body side member of claim 3, wherein the channels are distributed substantially homogeneously over the embossed distal surface of the release liner.

5. The body side member of claim 3, wherein the channels have a first volume and the interconnected cavities have a second volume, and the first volume is larger than the second volume.

6. The body side member of claim 2, wherein the reservoir has an openable outlet in liquid communication with the at least one channel.

7. The body side member of claim 2, wherein the reservoir has an outlet in liquid communication with the at least one channel, and the outlet is closed by one of a rupturable seal and a membrane.

8. The body side member of claim 1, wherein the distal surface of the release liner has an outer peripheral zone, and the outer peripheral zone is embossed with the plurality of interconnected cavities and configured to overlay the second zone of the adhesive layer.

9. The body side member of claim 1, wherein the distal surface of the release liner has an inner peripheral zone, and the inner peripheral zone is embossed with the plurality of interconnected cavities and configured to overlay the first zone of the adhesive layer.

10. The body side member of claim 1, wherein the distal surface of the backing layer comprises a first half of a coupling for coupling the body side member to a stomal output collecting bag.

11. The body side member of claim 1, further comprising:
   a stomal output collecting bag connected to the distal surface of the backing layer of the body side member.

12. The body side member of claim 1, further comprising a cover layer secured to a proximal surface of the release liner to form an enclosure between the cover layer and the release liner, and an absorbent moisture indicator contained in the enclosure.

* * * * *